US009847702B2

(12) United States Patent
Lambert et al.

(10) Patent No.: US 9,847,702 B2
(45) Date of Patent: Dec. 19, 2017

(54) IN-SITU METHOD FOR SEALING FLUID COOLED CONDUITS FOR A GENERATOR

(71) Applicant: General Electric Company, Schenectady, NY (US)

(72) Inventors: James Oldham Lambert, Roswell, GA (US); Eric Lawrence Schilf, Frankfort, IL (US)

(73) Assignee: General Electric Company, Schenectady, NY (US)

( * ) Notice: Subject to any disclaimer, the term of this patent is extended or adjusted under 35 U.S.C. 154(b) by 343 days.

(21) Appl. No.: 14/732,854

(22) Filed: Jun. 8, 2015

(65) Prior Publication Data

US 2016/0359396 A1    Dec. 8, 2016

(51) Int. Cl.
| | | |
|---|---|---|
| *H02K 15/00* | (2006.01) | |
| *B23K 37/02* | (2006.01) | |
| *G01N 21/954* | (2006.01) | |
| *H02K 15/12* | (2006.01) | |
| *B23K 31/12* | (2006.01) | |

(Continued)

(52) U.S. Cl.
CPC ......... *H02K 15/0093* (2013.01); *B23K 31/12* (2013.01); *B23K 31/125* (2013.01); *B23K 37/0276* (2013.01); *G01N 21/954* (2013.01); *H02K 3/22* (2013.01); *H02K 15/00* (2013.01); *H02K 15/0006* (2013.01); *H02K 15/125* (2013.01); *B23K 1/20* (2013.01);
(Continued)

(58) Field of Classification Search
CPC ............... H02K 15/00; H02K 15/0006; H02K 15/0093; H02K 15/125; H02K 3/22; B23K 1/20; B23K 31/12; B23K 31/125; B23K 37/0276; G01N 21/954; G01N 21/9548; Y10T 29/49009; Y10T 29/49769
See application file for complete search history.

(56) References Cited

U.S. PATENT DOCUMENTS 3,112,415 A    11/1963  Bahn et al.
3,693,036 A     9/1972  Schmitt
(Continued)

FOREIGN PATENT DOCUMENTS

JP          2010150973 A   *  7/2010

OTHER PUBLICATIONS

Joseph A. Worden & Jorge M. Mundulas, "Understanding, Diagnosing, and Repairing Leaks in Water-Cooled Generator Stator Windings", Aug. 2001, p. 1-24, GE Power Systems GER-3751A, USA.

*Primary Examiner* — A. Dexter Tugbang
(74) *Attorney, Agent, or Firm* — James W. Pemrick; Ernest G. Cusick; Frank A. Landgraff

(57) ABSTRACT

A method for sealing fluid cooled conduits in-situ for a generator is provided. The fluid or liquid cooled conduits are located external to a stator of the generator and substantially outward of stator bars. The method includes draining coolant from the fluid cooled conduits, and drying interior surfaces of the fluid cooled conduits. In inserting step inserts a borescope and a sealant applicator through an opening in one of the fluid cooled conduits. A locating step locates a brazed joint in the fluid cooled conduit, and a positioning step positions the borescope and the sealant applicator near the brazed joint. An applying step applies a sealant to the inside of the fluid cooled conduit at the brazed joint A viewing step may be used to view the brazed joint with the borescope to confirm that the applying step has been successful.

20 Claims, 7 Drawing Sheets

(51) Int. Cl.
*H02K 3/22* (2006.01)
*B23K 1/20* (2006.01)

(52) U.S. Cl.
CPC . *G01N 2021/9548* (2013.01); *Y10T 29/49009* (2015.01); *Y10T 29/49769* (2015.01)

(56) References Cited

U.S. PATENT DOCUMENTS

| | | | |
|---|---|---|---|
| 4,803,028 | A | 2/1989 | Torossian et al. |
| 5,350,815 | A | 9/1994 | Markovitz et al. |
| 5,605,590 | A | 2/1997 | Manning et al. |
| 5,717,267 | A * | 2/1998 | Paroz ............... H02K 3/22 310/260 |
| 6,778,053 | B1 | 8/2004 | Irwin et al. |
| 6,916,502 | B2 | 7/2005 | Moore et al. |
| 7,150,091 | B2 | 12/2006 | Mall et al. |
| 7,276,134 | B2 | 10/2007 | Rowe |
| 7,417,341 | B2 | 8/2008 | Mall et al. |
| 2006/0038988 | A1* | 2/2006 | Thermos ............ G01N 21/954 356/241.1 |
| 2013/0070240 | A1* | 3/2013 | Crann, Jr. ........... G01N 21/954 356/241.1 |

* cited by examiner

IN-SITU METHOD FOR SEALING FLUID COOLED CONDUITS FOR A GENERATOR

BACKGROUND OF THE INVENTION

The method described herein relates generally to an in-situ method for sealing fluid cooled conduits. More specifically, the method relates to an in-situ method for sealing brazed joints in fluid cooled conduits for a generator.

It is known that the windings of a dynamoelectric machine stator can be more effectively cooled by causing a dielectric fluid such as deionized water to flow through the windings inside the main insulation, such as in hollow strands of a multi-strand conductor bar. In a dynamoelectric machine stator winding, usually more than one of these insulated conductor bars lie in each slot formed in the laminated stator core. Very often, two such bars are employed, the top or radially inner bar in the slot being subjected to greater ohmic losses, and hence greater generation of heat, than the bottom or radially outer bar. It has also been known that the temperature difference between top and bottom bar can be reduced by the use of a two-pass system where the fluid flows through the length of the machine in a top bar and then returns through the machine in a bottom bar. Thus, the coolest fluid flows through the top bar with its greater heat losses and, after the temperature of the fluid has been raised somewhat, it returns through a bottom bar which has less heat losses. In this manner, the temperature difference between the top and bottom bars is reduced.

In a two-pass system, the fluid pressure drop in the restricted flow passages can result in large pumping losses in a large machine. Thus it has also been known to use a single-pass system wherein the fluid supplied at a series loop, electrically connecting top and bottom bars at one end of the machine, flows through top and bottom bars in parallel and is collected at the series loop at the other end of the machine, to be re-cooled and recirculated. However, with this arrangement, since fluid of the same temperature is supplied to both top and bottom bars, the top bar will be at a greater average temperature than the bottom bars. Therefore, changes in load on the machine, and the start-up and shutdown cycles, can cause relative movement between the bars in a slot due to differential thermal expansion and contraction, which causes abrasion and damage to the insulation.

In large generators, the windings are such that the terminating ends or phase leads of a group of connected coils forming a phase winding are disposed at circumferentially spaced locations about the periphery at one end of the core. The connections are such that a top bar can be electrically connected with a bottom bar of the same phase, located approximately 120 electrical degrees away, by means of an arcuate conductor called a connection ring. The connection ring is also electrically connected through lower leads to bushings leading through the casing. For a three-phase generator, there would ordinarily be six such connection rings, six lower leads, and six bushings disposed on one end of the generator. The connection rings and the lower leads carry substantial currents and must also be cooled. This also may be done by cooling internal passages with a fluid.

The hollow conductors external to the stator include the phase leads, series loops and connection rings. Typically, deionized water is passed through these hollow conductors/conduits. During manufacture of the phase leads, series loops and connection rings many brazed joints are required to connect the various conductors/conduits and fittings. These brazed joints often contain phosphorus, and the combination of phosphorous and water may result in corrosion and subsequently leaks. It will be appreciated that water leaking in or around a utility scale generator is not desired. If the brazed joints are failing or leaks are detected, one option is to completely replace all the phase leads, series loops and connection rings. Unfortunately, this approach is very expensive and time consuming. New parts will have to be purchased, which can take many months to procure and manufacture, and these parts may take days or even a week to install.

BRIEF DESCRIPTION OF THE INVENTION

In an aspect of the present invention, a method for sealing fluid cooled conduits in-situ for a generator is provided. The fluid or liquid cooled conduits are located external to a stator of the generator and substantially outward of stator bars. The method includes draining coolant from the fluid cooled conduits, and drying interior surfaces of the fluid cooled conduits. In inserting step inserts a borescope and a sealant applicator through an opening in one of the fluid cooled conduits. A locating step locates a brazed joint in the fluid cooled conduit, and a positioning step positions the borescope and the sealant applicator near the brazed joint. An applying step applies a sealant to the inside of the fluid cooled conduit at the brazed joint A viewing step may be used to view the brazed joint with the borescope to confirm that the applying step has been successful.

In another aspect of the present invention, a method for sealing fluid cooled conduits in-situ for a generator is provided. The fluid or liquid cooled conduits are located external to a stator of the generator and substantially outward of stator bars. The method includes the steps of inserting a borescope and an epoxy applicator through an opening in one of the fluid cooled conduits, locating a brazed joint in the fluid cooled conduit, and positioning the borescope and the epoxy applicator near the brazed joint. An applying step applies an epoxy to an inside of the fluid cooled conduit at the brazed joint. The locating, positioning, and applying steps are repeated until a desired number of brazed joints have been coated with epoxy and sealed. The method is performed on the generator in-situ.

In yet another aspect of the present invention, a method is provided for sealing fluid cooled conduits in-situ for a generator. The fluid or liquid cooled conduits are located external to a stator of the generator and substantially outward of the stator bars. The method includes the steps of inserting a borescope and a powder coat painting applicator through an opening in one of the fluid cooled conduits, locating a brazed joint in the fluid cooled conduit, positioning the borescope and the powder coat painting applicator near the brazed joint, and applying a powder coat paint to an inside of the fluid cooled conduit at the brazed joint. A repeating step is used for repeating the locating, positioning, and applying steps until a desired number of brazed joints have been coated with the powder coat paint and sealed. The method is performed on the generator in-situ.

DETAILED DESCRIPTION OF THE INVENTION

One or more specific aspects/embodiments of the present invention will be described below. In an effort to provide a concise description of these aspects/embodiments, all features of an actual implementation may not be described in the specification. It should be appreciated that in the development of any such actual implementation, as in any engineering or design project, numerous implementation-specific decisions must be made to achieve the developers' specific goals, such as compliance with machine-related, system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a", "an", and "the" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "one aspect" or "an embodiment" or "an aspect" of the present invention are not intended to be interpreted as excluding the existence of additional embodiments or aspects that also incorporate the recited features.

Figure 1:
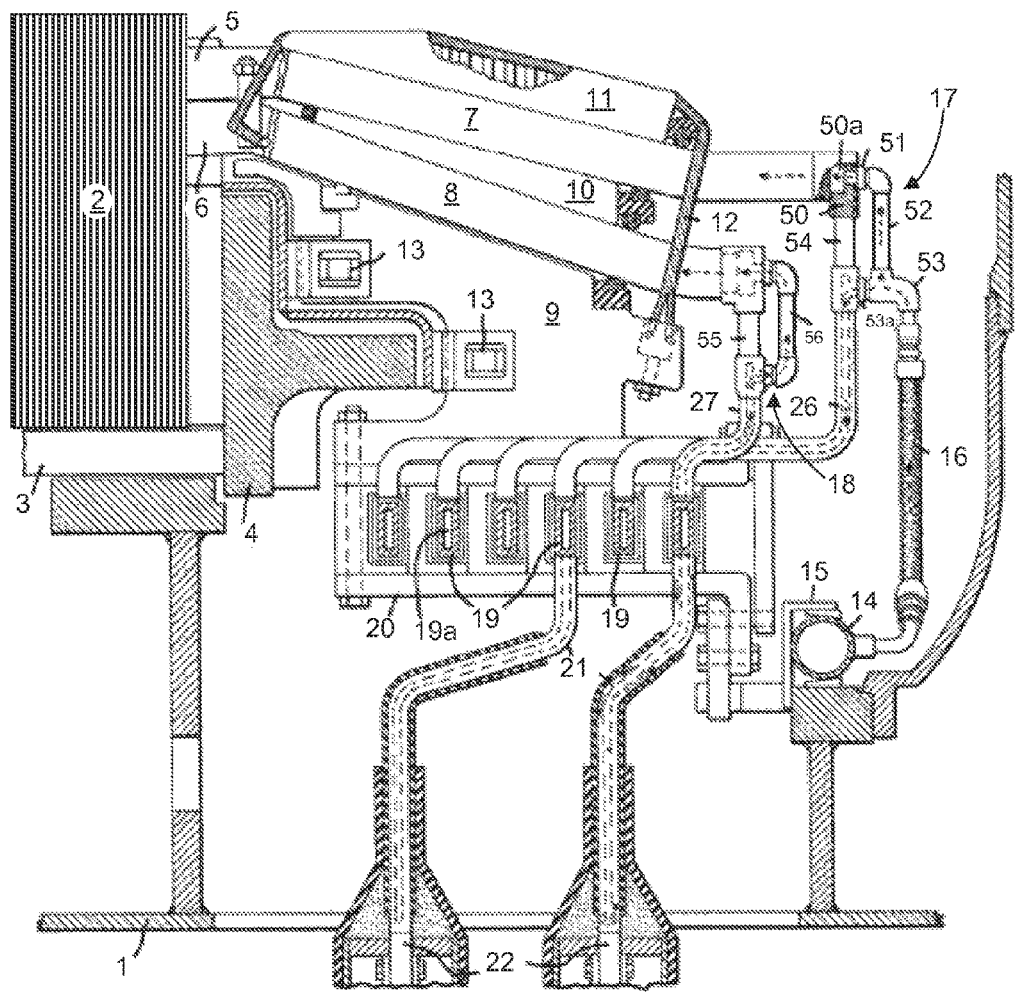
FIG. 1 illustrates a horizontal elevation, partly in section, of the lower portion of a generator stator in the end turn region, taken at the location of the phase leads, series loops and connection rings.

Referring to FIG. 1 and the construction of one known generator, an outer gas-tight wrapper 1 contains a supply of hydrogen gas used to cool the rotor (not shown) and portions of the stator 2. Stator 2 comprises laminations held in place by an inner cage 3 and circumferential end flanges 4. The top (or radially inner) armature bars 5 and the bottom (or radially outer) armature bars 6 extend from slots in stator 2 into the end turn region. Top bars 5 and bottom bars 6 are bent circumferentially in opposite directions as they emerge from the slot and are formed with a complex curvature to lie along a frusto-conical surface. At most locations, they are simply connected together at a series loop to form a complete turn. However, at circumferentially spaced locations around the stator periphery, they terminate at extending phase leads 7, 8 where they are connected to the connection rings 19. In FIG. 1, the ends of a top phase lead bar 7 and a bottom phase lead bar 8 are shown, although it is understood that these bars have been rotated from their actual positions into the plane of the drawing so as to show their continuity from the slots. It is to be understood that the stator, for the purposes of this description, stops at the interface between top/bottom bars 5, 6 and the phase leads 7, 8. Accordingly for this disclosure, the phase leads 7, 8, series loops 17, 18 and connection rings 19 are all considered to be fluid cooled conduits and located external to the stator. Fluid is defined as a liquid (such as water or other liquid coolant) or a gas.

The end turns of the winding are supported in a cage structure comprising circumferentially spaced, axially extending outer support members 9, intermediate spacer members 10 and inner support members 11. Inner members 11 and outer members 9 hold the phase leads between them by means of a tension strap, such as a resin impregnated glass fiber rope 12. Outer members 9 are mounted so as to be axially slidable with respect to the end flange 4 by means of slidable fittings 13.

Fluid coolant is supplied from a source of fluid coolant under pressure (not shown) to an inlet header 14, which is a hollow circular pipe supported by suitable means such as the bracket 15. A similar outlet header at the other end of the machine collects the spent coolant, after which the coolant is cooled and recirculated and, after suitable processing, depending upon the type of coolant, is pumped back to inlet header 14 in a continuous cooling circuit. The fluid coolant is supplied to the armature conductor bars through a number of circumferentially spaced insulating hoses, such as the one shown at 16, either to the series loops 17, 18 or to the phase leads 7, 8. Hoses 16 may be a solid polytetrafluoroethylene or a multilayer structure of flexible insulating material reinforced to prevent collapse. They serve to insulate the windings from ground, while supplying fluid thereto. As one example only, hoses 16 may be comprised of polytetrafluoroethylene (PTFE), or Teflon ® (a registered trademark of E. I. du Pont de Nemours and Company).

A fluid coolant is also furnished to the bottom phase leads 8 by means of a group of fittings indicated generally as 18. The group of fittings 18 may also be referred to as a series loop. However, series loops do not occur at the phase connections, instead series loops occur where there is no phase connection. A portion of the fluid also flows through the leads 26, 27 which connect top and bottom phase leads 7, 8 respectively to the connection rings 19. Connection rings 19 have internal cooling passages 19a and are held in suitable brackets 20 attached to the outer supporting members 9 so as to be axially slidable with the end turn supporting cage. Lower leads 21 are electrically and hydraulically connected to two corresponding connection rings 19. The lower leads 21 extend downward to connect with the main leads 22 leading to the bushings (not shown).

Looking first at the series loop 17 for top phase lead 7, it will be seen that the hollow strands pass through an aperture in the walls of a conductive box 50, and are electrically connected thereto with a leak-tight connection such as by brazing. The interior 50a of box 50 communicates with a pipe fitting 51 and a connecting pipe 52. Pipe 52 is connected to a T fitting 53 supplied by one of the insulated hoses 16. Fluid from the other outlet of T fitting 53, instead of passing directly to a bottom bar, is hydraulically joined to the lead 26 by means of a pipe fitting 53a. Although the top phase lead 7 and the lead/conduit 26 are supplied in parallel with fluid from the T fitting 53, they are directly connected electrically by means of copper straps 54 brazed therebetween. The bottom phase lead 8 is supplied with fluid by means of a similar series loop 18. Lead 27 is electrically connected to the box of series loop 18 by means of copper straps 55, as before, while the fluid bypasses straps 55 through a pipe 56 to enter the box by means of a piped connection 56, as will be apparent from the drawing.

Figure 2:
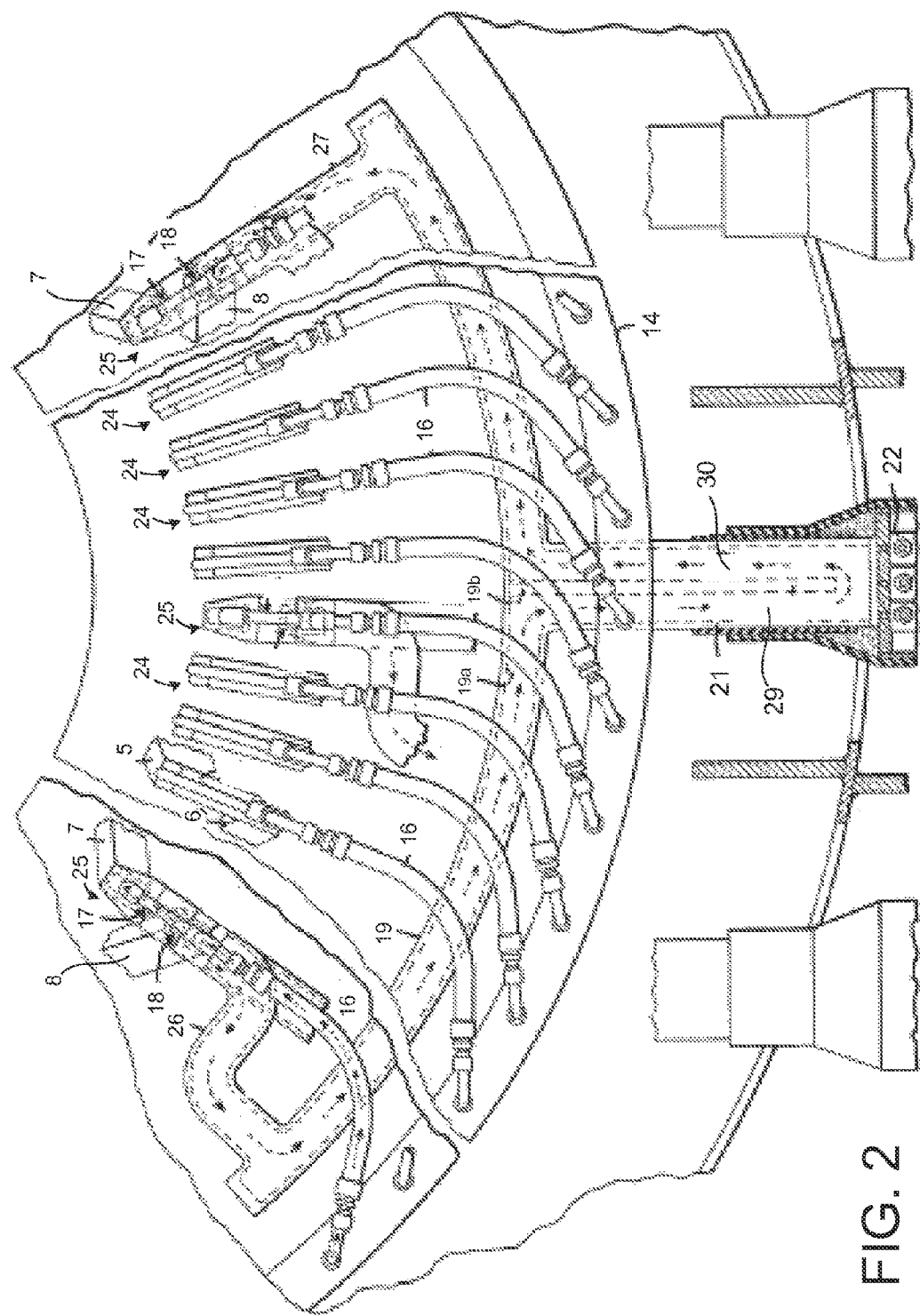
FIG. 2 illustrates a partial end view of the fluid cooled conduits shown in FIG. 1, but showing only one connection ring and one lower lead, the rest being omitted for clarity.

FIG. 2 illustrates a partial end view of the fluid cooled conduits shown in FIG. 1, but showing only one connection ring and one lower lead, the rest being omitted for clarity. FIG. 2 shows only one such connection ring and lower lead, in order to clarify the description, but it will be understood that a similar arrangement is used for each of the other connection rings and lower leads. It is also understood that phase leads connected by a connection ring will be of the same electrical phase. Also, since the top and bottom phase leads which are connected by one connection ring are circumferentially spaced approximately 120 electrical degrees, the drawing is broken away in segments to indicate this. Most of the end turns themselves and the end turn supporting structure are omitted for clarity.

Each of the insulating hoses 16 supplies cooling fluid for a complete coil consisting of top and bottom bars. Most coils are supplied through series loops indicated generally as 24. At several circumferentially-spaced locations, however, a group of special phase lead fittings shown generally at 25, are employed. The phase lead fitting group 25 consists of the two series loops 17 and 18 (see FIG. 1). At these locations, hoses 16 supply fluid to series loop 17. Each series loop 17 divides the fluid into two portions. One portion flows through top phase lead 7, while the other portion flows through a lead 26 electrically connected to phase lead 7. The other end of lead 26 is electrically and hydraulically connected to the connection ring 19 which extends through an arc to join another similar lead 27. The top of lead 27 is both electrically and hydraulically connected by means of series loop 18 (see FIG. 1) to the circumferentially spaced bottom phase lead 8.

Figure 3:
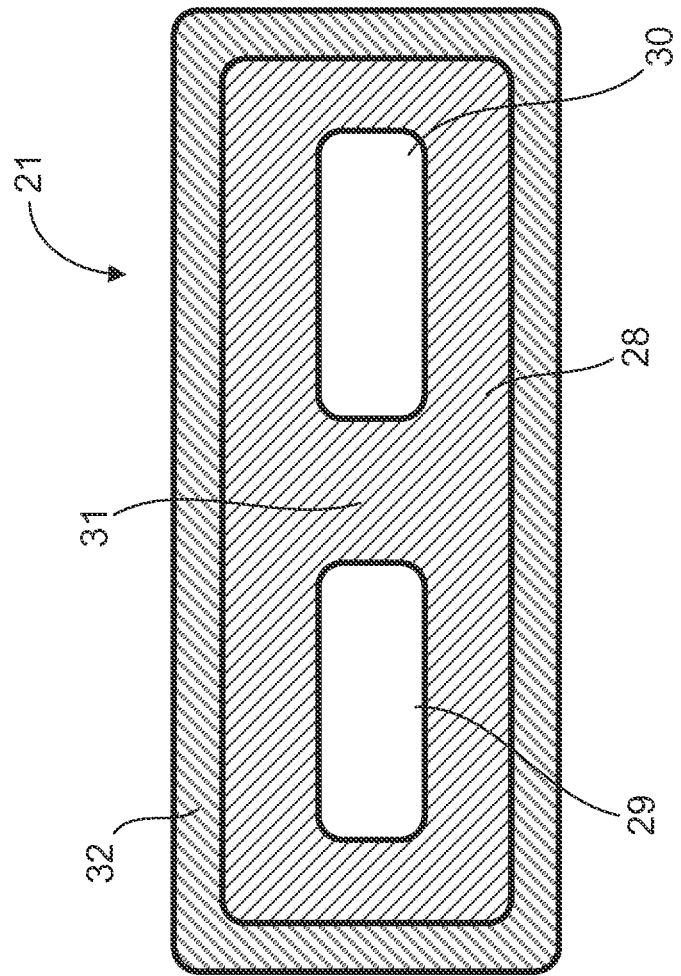
FIG. 3 illustrates an enlarged cross-section through a lower lead.

At some intermediate point on connection ring 19, the top of a lower lead 21 is electrically and hydraulically connected, with its lower end being connected to leads 22 and then to the high-voltage bushings. As indicated by the arrows in FIG. 2, the lower lead 21 is cooled by fluid flowing down toward the bushing and back again through two spaced passages. Referring to FIG. 3, which is a cross section taken through lead 21, indicates that it comprises a rectangular conductor bar 28 having two cooling passages 29, 30 spaced by a dividing web 31 and surrounded by insulation 32. A portion of the web 31 separating passages 29, 30 is cut away near the bottom to provide for a return flow of the fluid, as indicated in FIG. 2. At the top of lead 21, the fluid flow passages 29, 30 join the interior passage 19a in connection ring 19, while an obstruction 19b interrupts passage 19a. It will be apparent from tracing the arrows in FIG. 2 that fluid flows through lead 26, through a portion of connection ring 19, through lower lead 21, through the remainder of the connection ring 19, and thence through the lead 27. It is to be understood that the conduits, conductors and any electrical conductors may have rectangular or circular cross-sections. The lead 21 may also be square in cross section with a circular passage, rectangular in cross section with a single rectangular passage, or have any suitable configuration/cross section as desired in the specific application.

Figure 4:
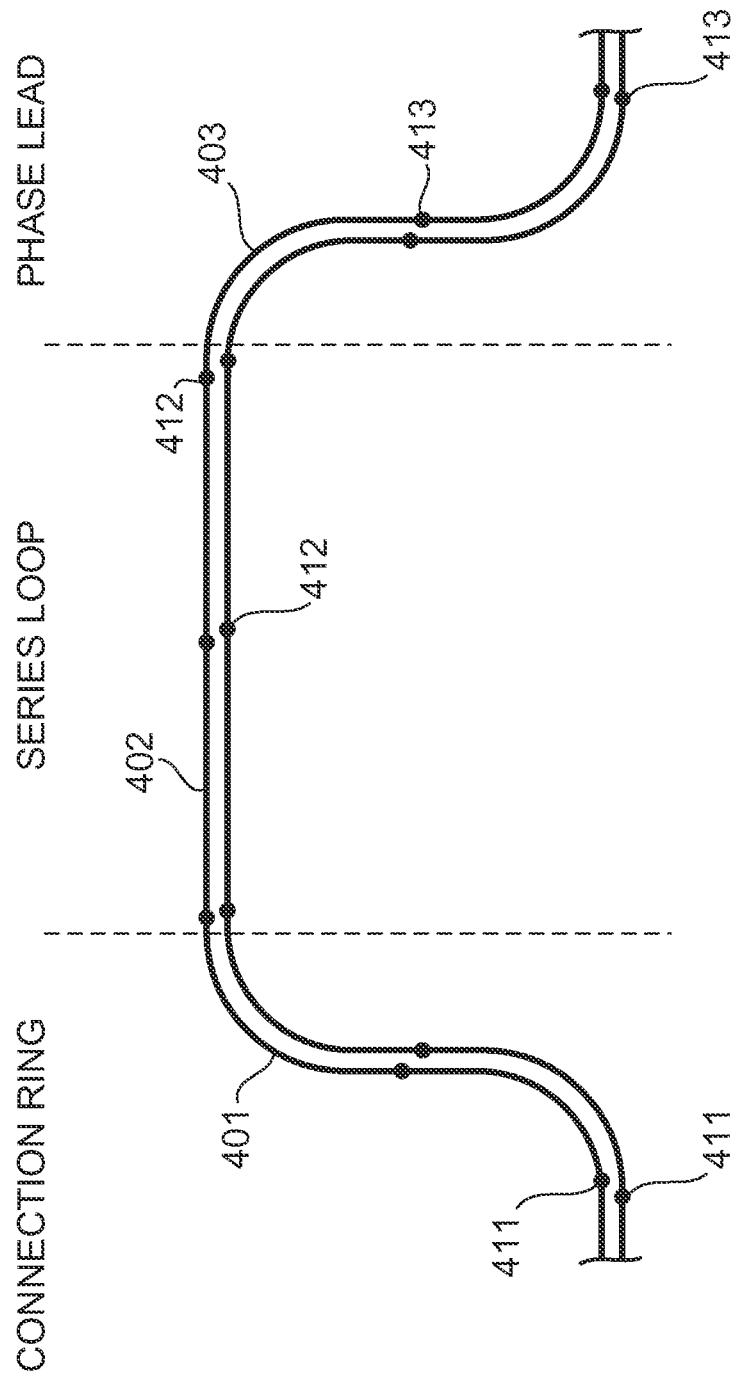
FIG. 4 illustrates a schematic view of fluid cooled conduits that are located external to the stator of a generator.

FIG. 4 illustrates a schematic view of fluid cooled conduits that are located external to the stator of a generator. The fluid cooled conduits may include the connection rings 401 (equivalent to connection ring 19 in FIGS. 1-2), series loops 402 (equivalent to series loops 17, 18) and phase leads 403 (equivalent to phase leads 7 and 8). These conduits also contain many brazed joints 411, 412 and 413 that join different conduit sections together or various fittings to the conduits. The brazed joints 411, 412 and 413 typically contain a phosphorous containing braze alloy and over time some of these phosphorous containing brazed joints may develop leaks. According to aspects of the present invention, a method is provided to seal these brazed joints 411, 412 and 413 from inside of the fluid filled conduits by applying a sealant to the brazed joints. The sealant may be an epoxy or a powder coat paint, to be more fully described hereafter.

Figure 5:
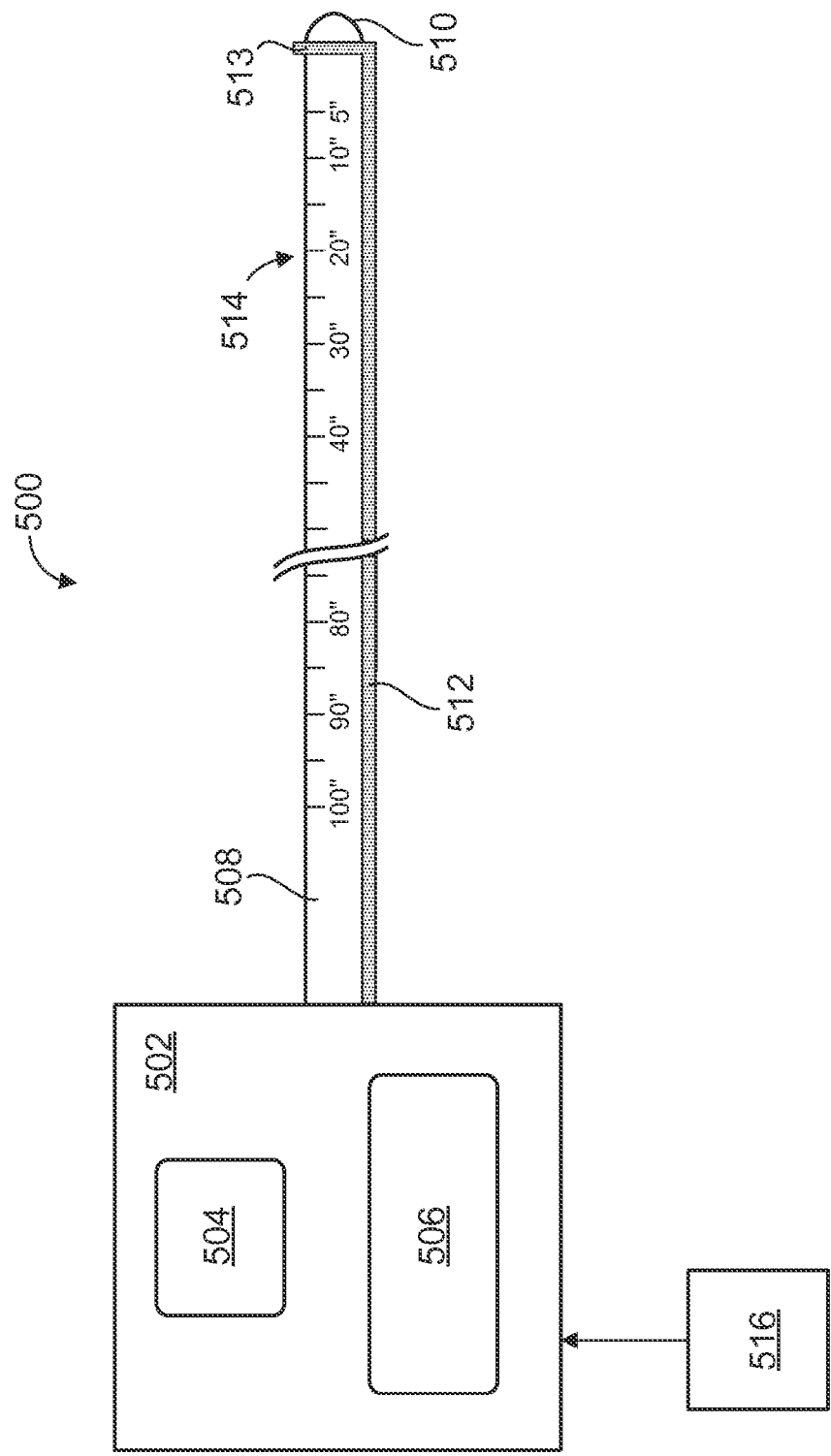
FIG. 5 illustrates a simplified schematic view of a borescope and sealant applicator system, according to an aspect of the present invention.

FIG. 5 illustrates a simplified schematic view of a borescope and sealant applicator system, according to an aspect of the present invention. The borescope 500 may include a control panel 502 having a display 504 and input device 506. The display 504 may be used to view the interior of the fluid cooled conduits of the generator. The input device 506 may take the form of a keyboard, joystick, touchpad or any other suitable interface and control device. The input device may be used to control movement of and functioning of the flexible cable 508. Flexible cable 508 is configured to be inserted into the fluid cooled conduits and may be any suitable length as required by the specific application. The flexible cable 508 includes an imaging lens or camera 510 and a supply of sealant 512 and a sealant applicator 513. In addition, the flexible cable may include readable indicia 514 that indicate the depth of insertion within the fluid filled conduits. As one example only, indicia 514 may be printed marks indicating depth in inches (as shown), or the indicia may be in foot, meters, centimeters or any suitable measurement scale as desired. The sealant may be drawn from a sealant supply 516, routed along supply tube 512 and sprayed onto the brazed joint by spray head or applicator 513. The spray head 513 may be configured to spray in a 360 degree pattern or to spray and rotate to cover the entire internal cylindrical shape of the brazed joint.

The sealant may be an epoxy or a powder coat paint. For an epoxy, an epoxy resin may be applied in two parts for penetration and wet-out followed by a higher viscosity modification of the same fluid epoxy resin. Thus, an initial or first part of the fluid epoxy resin of low viscosity is applied to the brazed joint and which applied resin may readily flow into the various interstices of the brazed joint into which the epoxy is applied. The second part of the resin has a greater viscosity than the first part and is applied in overlying relation to the first part to form a barrier seal between the fluid coolant in the conduit and the brazed joint and particularly the brazed alloy. The fluid epoxy resin may be of the type described in U.S. Pat. No. 5,350,815, of common assignee herewith, the disclosure of which U.S. patent is incorporated herein by reference in its entirety. It will also be appreciated that other types of resins may be utilized for example those identified in U.S. Pat. No. 5,605,590, of common assignee herewith, the disclosure of which U.S. patent is incorporated herein by reference in its entirety. In addition, the epoxy may also be applied in a one step or one layer process. It will be appreciated that other types of resins may be utilized instead. For example, other fluid epoxy resins may include those based on the diglycidyl ether of bisphenol A such as Epon 826 and Epon 828 made by Shell Chemical Co. and other similar resins made by other manufacturers such as Dow Chemical Co. and Ciba Chemical Co.; fluid bisphenol F diglycidyl ether epoxy resins such as Epon DPL-862 (Shell Chemical Co.) or Araldite GY 281 and Araldite GY 308 (Ciba Chemical Co.). Offsets of any of the epoxy resins made by other manufacturers, mixtures of epoxy resins or epoxy resins modified with reactive diluents can also be used. The epoxies also include an additive to make the resins of a particular color, for example, white, for ready visibility against the copper during the repair. A titanium oxide is used as a satisfactory additive.

In powder coating, a powdered media is applied by electrostatically charging the powdered material and spraying it onto the part. The part is then heated and the powder particles melt to form a continuous film. Powders for powder coating may be either thermoplastic powders which will re-melt on heating or thermosetting powders which do not re-melt on reheating. With thermosetting powders, during the curing process, a chemical cross-linking reaction is triggered at the curing temperature and reduces chemical reaction which gives the powder coating many of its desirable properties. Ultraviolet-curable powder coatings, which are applied in the same manner as conventional powder coatings, offer some advantages including shorter cure time or lower cure temperature or both and are thus considered an appropriate alternative to conventional heat curing powders. Examples of suitable powder resins include epoxy powder resins, silicone powder, and silicone hybrid resin systems (silicone/epoxies and silicone/acrylics), examples of which are disclosed in U.S. Pat. No. 6,778,053, of common assignee herewith, the disclosure of which is incorporated herein by reference in its entirety.

Figure 6:
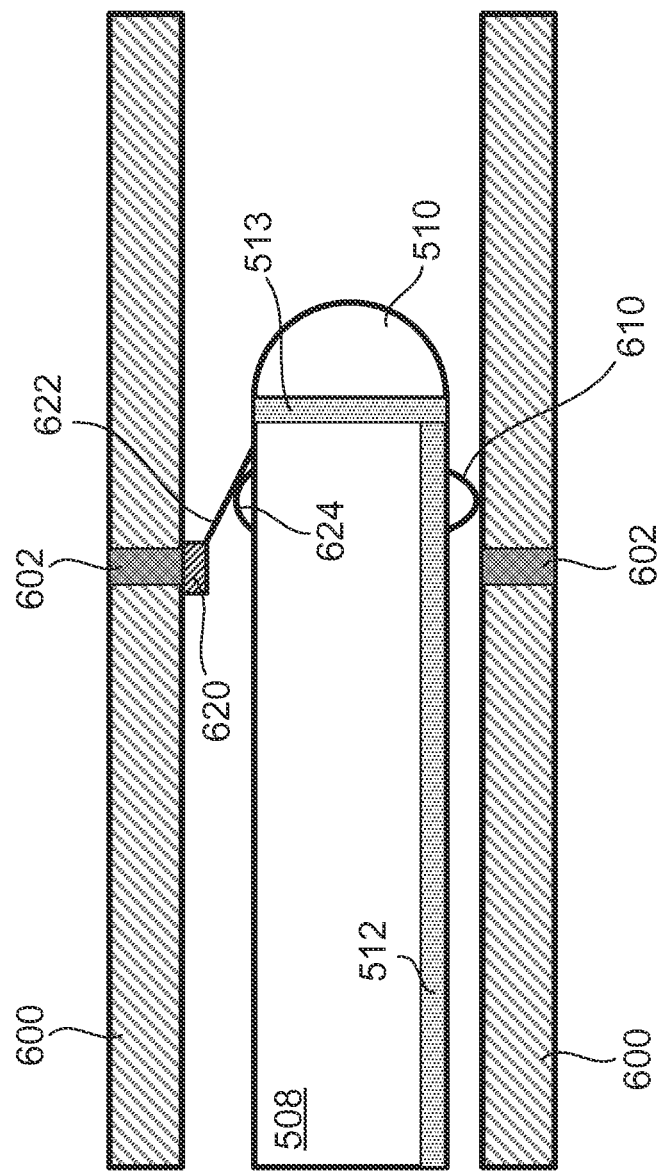
FIG. 6 illustrates an enlarged, cross-sectional view of the borescope and sealant applicator inserted into a fluid cooled conduit, according to an aspect of the present invention.

FIG. 6 illustrates an enlarged, cross-sectional view of the borescope and sealant applicator inserted into a fluid cooled conduit, according to an aspect of the present invention. The fluid cooled conduit 600 may comprise the connection rings 19, series loops 17, 18 and/or the phase leads 7, 8, or any other suitable conduit or fitting external to the stator, and one or more brazed joints 602. The brazed joints 602 may be experiencing leaks or prone to leak, so the sealant will prevent further leakage. The borescope may include one or more springs 610, and the springs help to center the flexible cable 508 as it travels along the fluid cooled conduit 600. The inside of the fluid cooled conduit 600 may be scanned with a scanner 620, such as a non-destructive transducer or an ultrasonic transducer. The scanner 620 is in communication with control panel 502 or any other suitable display/interface device. As the scanner 620 slides along the inside of the conduit, the signal will vary when it passes over a brazed joint 602. This change in signal identifies the location of the brazed joint 602. For example, when the signal slides along a solid copper pipe, the signal will be relatively constant. However, when it transitions over to a brazed joint between two joined copper sections, the braze alloy will cause the scanner to return a slightly different signal or waveform. This resulting change indicates the location of the brazed joint. The distance from the scanner 620 to the applicator 513 is known, so once the brazed joint is found the flexible cable 508 may be slid back by the appropriate distance and then activated to cover and seal the brazed joint. The flexible cable can be slid back a bit more so that the camera 510 can view and verify the sealing operation. As one example only, the predetermined distance between scanner 620 and applicator 513 may be about three inches, however, any suitable distance may be employed as desired. In addition, the scanner 620 may be supported and deployed or retracted by an extending arm 622 and spring 624. The arm 622 and spring 624 may be configured to retract into flexible cable 508 when not in use, and to deploy radially outward to bias the sensor against the interior of the conduit 600 when scanning is desired.

Figure 7:
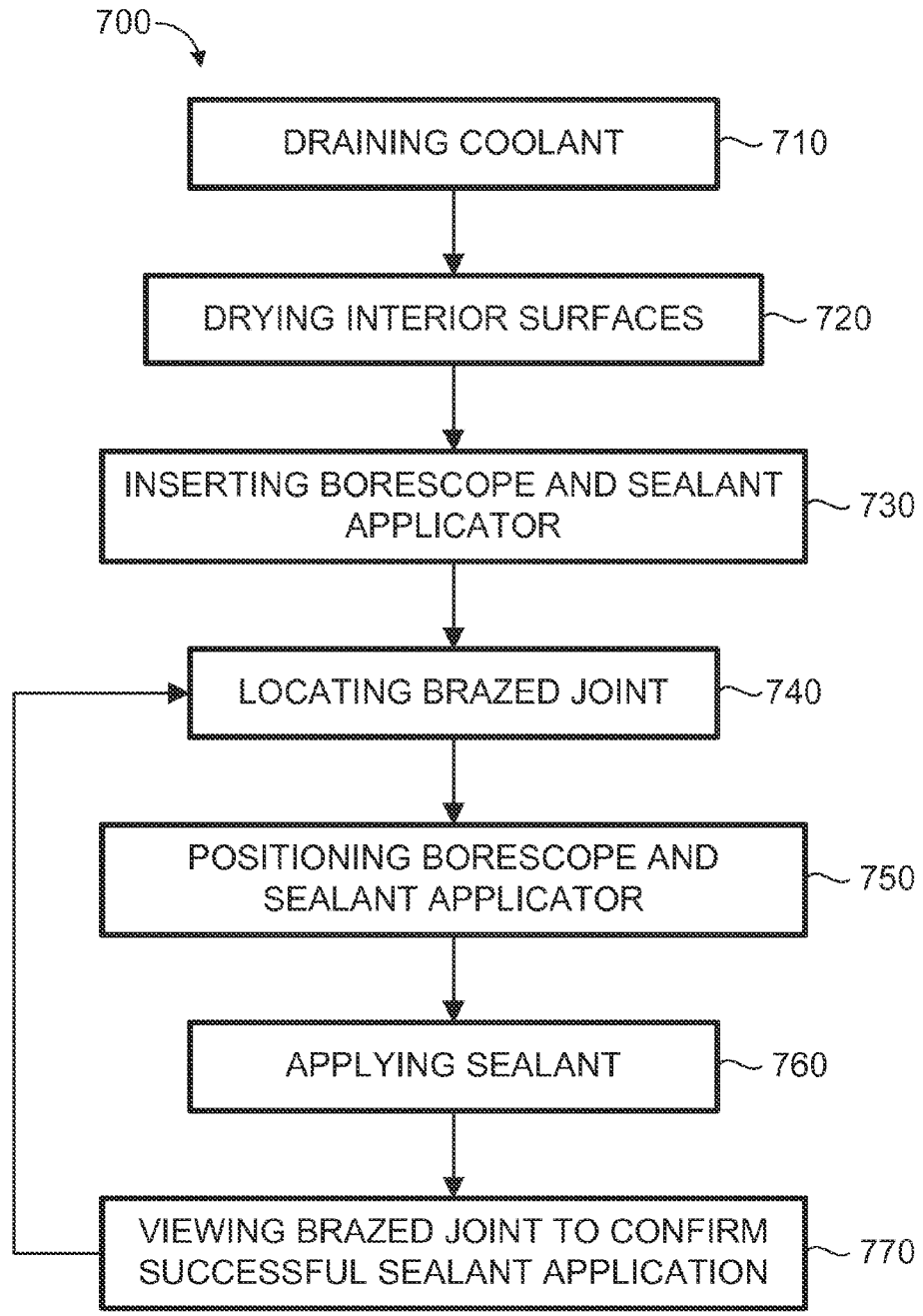
FIG. 7 is a flowchart of an in-situ method for sealing fluid cooled conduits of a generator, according to an aspect of the present invention.

FIG. 7 is a flowchart of an in-situ method for sealing fluid cooled conduits of a generator, according to an aspect of the present invention. The method 700 seals fluid cooled conduits 7, 8, 17, 18, 19 in-situ for a generator. The fluid cooled conduits 7, 8, 17, 18, 19 are located external to a stator of the generator and substantially outward of stator bars. The fluid cooled conduits may include the phase leads 7, 8, series loops 17, 18, connection rings 19 and any other fittings or conduits located external to the stator 2. The method 700 includes a draining step 710 that drains coolant from the fluid cooled conduits. For example, inlet header 14 may be disconnected so that the coolant can be drained from the generator or at least the fluid cooled conduits external to the stator. An important feature is that the fluid cooled conduits remain substantially in place and in-situ, except for that which is needed to remove and drain the coolant. After the draining step 710 a drying step 720 is used for drying the interior surfaces of the fluid cooled conduits. For example, the drying step may include applying a vacuum to the inside of the fluid cooled conduits. The vacuum will "boil off" and remaining fluid coolant. The term vacuum is defined as a negative or reduced pressure, or a state where air has been completely or partly removed.

An inserting step 730 inserts a borescope 508 and a sealant applicator 513 through an opening in one of the fluid cooled conduits. For example, the borescope could be inserted into inlet header 14, series loops 17, 18, phase rings 7, 8, connection rings 19, lower leads 21, main leads 22 or any other desired entry point. As one example only, flexible cable 508 may be inserted into inlet header 14, and then hose 16, followed by series loop 17 and finally into phase lead 7. A locating step 740 locates a brazed joint 602 in the fluid cooled conduit. The location may be determined by known predetermined locations of the brazed joints. For example, the distance of each brazed joint may be known from inlet header 14, so the flexible cable may be inserted a known distance/depth (e.g., 150"), at which point the insertion is stopped and the location may be viewed with the camera 510. Alternatively, the inside of the fluid cooled conduit 600 may be scanned with an ultrasonic transducer 620, the output of which is monitored and where a brazed joint 602 location is identified by a predetermined signal from the ultrasonic transducer. A positioning step 750 positions the borescope and the sealant applicator near the brazed joint. As described previously, once the brazed joint location is known the borescope may be positioned near the brazed joint.

An applying step 760 applies a sealant to an inside of the fluid cooled conduit at the brazed joint. The sealant may be an epoxy or a powder coat paint. In practice, it may be desired to locate and seal the deepest braze joints first. In this manner the borescope and flexible cable 508 are withdrawn from coated joints as the sealing method progresses. For example if there were brazed joints at depths of 50", 100" and 150", then the 150" deep brazed joint would be located and sealed first. The flexible cable could be retracted to the 100" deep brazed joint at which point this brazed joint is sealed, followed lastly by the 50" brazed joint. A viewing step 770 views the brazed joint to confirm that the applying step 760 has been successful. The camera 510 is used to image the sealant site and to confirm that sealant application is satisfactory. If sealant coverage is unsatisfactory that additional sealant may be applied until the desired result is obtained. The locating step 740, positioning step 750, applying step 760 and viewing step 770 are repeated until a desired number of brazed joints have been sealed.

One of the advantages provided by the method of the present invention is that the fluid cooled conduits (e.g., phase leads, series, loops, connection rings, fitting, etc.) that are located external to the stator may be sealed in-situ. This enables the method to be performed without having to disassemble a majority of the stator or its associated fluid cooled conduits. In addition, the time required for taking the generator off-line is greatly reduced when compared to total disassembly of the stator or installation of new fluid cooled conduits. The existing brazed joints can be sealed and refurbished in a shorter amount of time with less expense incurred by the generator operator/owner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for sealing fluid cooled conduits in-situ for a generator, the fluid cooled conduits located external to a stator of the generator and substantially outward of stator bars, the method comprising:
   draining coolant from the fluid cooled conduits; drying interior surfaces of the fluid cooled conduits;
   inserting a borescope and a sealant applicator through an opening in one of the fluid cooled conduits;
   locating a brazed joint in the fluid cooled conduit;
   positioning the borescope and the sealant applicator near the brazed joint;
   applying a sealant to an inside of the fluid cooled conduit at the brazed joint; and
   viewing the brazed joint with the borescope to confirm that the brazed joint has been sealed with the sealant.

2. The method of claim 1, the method further comprising:
   repeating the locating, positioning, applying and viewing steps until a desired number of brazed joints have been sealed.

3. The method of claim 1, the sealant comprising an epoxy or a powder coat paint and the fluid cooled conduits comprising at least one of:
   a connection ring, a series loop or a phase lead.

4. The method of claim 3, the drying step further comprising:
   applying a vacuum to the inside of the fluid cooled conduit.

5. The method of claim 4, the locating step further comprising:
   measuring a depth of an insertion of the borescope and the sealant applicator and comparing the depth to predetermined locations of brazed joints.

6. The method of claim 4, the locating step further comprising:
   scanning an inside of the fluid cooled conduit with an ultrasonic transducer;
   monitoring an output of the ultrasonic transducer; and
   wherein a location of the brazed joint is identified by a predetermined signal from the ultrasonic transducer.

7. A method for sealing fluid cooled conduits in-situ for a generator, the fluid cooled conduits located external to a stator of the generator and substantially outward of stator bars, the method comprising:
   inserting a borescope and an epoxy applicator through an opening in one of the fluid cooled conduits;
   locating a brazed joint in the fluid cooled conduit;
   positioning the borescope and the epoxy applicator near the brazed joint;
   applying an epoxy to an inside of the fluid cooled conduit at the brazed joint;
   repeating the locating, positioning, and applying steps until a desired number of brazed joints have been coated with epoxy and sealed, and wherein the method is performed on the generator in-situ.

8. The method of claim 7, the fluid cooled conduits comprising at least one of:
   a connection ring, a series loop or a phase lead.

9. The method of claim 8, further comprising:
   draining coolant from the fluid cooled conduits.

10. The method of claim 9, further comprising:
    drying interior surfaces of the fluid cooled conduits.

11. The method of claim 10, the drying step further comprising:
    applying a vacuum to the inside of the fluid cooled conduit.

12. The method of claim 11, further comprising:
    viewing the brazed joint of the desired number of brazed joints to confirm that the brazed joint has been sealed with the epoxy.

13. The method of claim 12, the locating step further comprising:
    measuring a depth of an insertion of the borescope and the epoxy applicator in the fluid cooled conduit and comparing the depth to predetermined locations of brazed joints.

14. The method of claim 12, the locating step further comprising:
    scanning the inside of the fluid cooled conduit with an ultrasonic transducer;
    monitoring an output of the ultrasonic transducer; and
    wherein a location of the brazed joint is identified by a predetermined signal from the ultrasonic transducer.

15. A method for sealing fluid cooled conduits in-situ for a generator, the fluid cooled conduits located external to a stator of the generator and substantially outward of stator bars, the method comprising:
    inserting a borescope and a powder coat painting applicator through an opening in one of the fluid cooled conduits;
    locating a brazed joint in the fluid cooled conduit;
    positioning the borescope and the powder coat painting applicator near the brazed joint;
    applying a powder coat paint to an inside of the fluid cooled conduit at the brazed joint; and
    repeating the locating, positioning, and applying steps until a desired number of brazed joints have been coated with the powder coat paint and sealed, and wherein the method is performed on the generator in-situ.

16. The method of claim 15, the fluid cooled conduits comprising at least one of:
    a connection ring, a series loop or a phase lead.

17. The method of claim 16, further comprising:
    draining coolant from the fluid cooled conduits;
    drying interior surfaces of the fluid cooled conduits, the drying including applying a vacuum to the inside of the fluid cooled conduit.

18. The method of claim 11, further comprising:
    viewing the brazed joint of the desired number of brazed joints to confirm that the brazed joint has been sealed with the powder coat paint.

19. The method of claim 12, the locating step further comprising:

measuring a depth of an insertion of the borescope and the powder coat painting applicator in the fluid cooled conduit and comparing the depth to predetermined locations of brazed joints.

20. The method of claim 12, the locating step further comprising:
   scanning the inside of the fluid cooled conduit with an ultrasonic transducer;
   monitoring an output of the ultrasonic transducer; and
   wherein a location of the brazed joint is identified by a predetermined signal from the ultrasonic transducer.

* * * * *